US009572491B2

(12) United States Patent
Nakagawa et al.

(10) Patent No.: US 9,572,491 B2
(45) Date of Patent: Feb. 21, 2017

(54) VITAL SIGNAL MEASUREMENT DEVICE, AND VITAL SIGN SIGNAL MEASUREMENT SYSTEM

(75) Inventors: Tatsuo Nakagawa, Tokyo (JP); Tomoyuki Ishii, Tokyo (JP); Akira Kotabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/421,823

(22) PCT Filed: Sep. 3, 2012

(86) PCT No.: PCT/JP2012/072293
§ 371 (c)(1),
(2), (4) Date: Feb. 14, 2015

(87) PCT Pub. No.: WO2014/033942
PCT Pub. Date: Mar. 6, 2014

(65) Prior Publication Data
US 2015/0230706 A1    Aug. 20, 2015

(51) Int. Cl.
*G08C 19/22* (2006.01)
*A61B 5/00* (2006.01)

(52) U.S. Cl.
CPC ........... *A61B 5/0022* (2013.01); *A61B 5/0004* (2013.01); *A61B 5/0006* (2013.01)

(58) Field of Classification Search
CPC .... A61B 5/0022; A61B 5/0006; A61B 5/0004
USPC ............... 340/870.07, 5.1, 539.12
See application file for complete search history.

(56) References Cited

U.S. PATENT DOCUMENTS

| 8,814,792 B2* | 8/2014 | Raptis ............... A61B 5/002 340/539.11 |
| 2007/0135692 A1* | 6/2007 | Hwang ............... A61B 5/0002 600/301 |
| 2009/0192399 A1* | 7/2009 | Choi ............... A61B 5/02405 600/519 |
| 2011/0230774 A1 | 9/2011 | Kobayashi et al. |

FOREIGN PATENT DOCUMENTS

| CN | 1820703 A | 8/2006 |
| JP | 2008-178626 A | 8/2008 |
| JP | 2011-050546 A | 3/2011 |

OTHER PUBLICATIONS

Office Action dated Mar. 2, 2016 for related Chinese Application No. 201280075380.4.

* cited by examiner

*Primary Examiner* — Dhaval Patel
(74) *Attorney, Agent, or Firm* — Miles & Stockbridge P.C.

(57) ABSTRACT

A vital signal measurement system including a plurality of terminals aims to facilitate synchronization of each terminal with respect to other terminals. Each of the plurality of terminals (102) is provided with a first vital signal sensor (201) for measuring a vital signal, a first memory (205) for storing a first data which is based on the vital signal, and a first radio communication unit (206) for communicating with other terminals by radio. The first data is applied with a sequence number corresponding to the first data and the number indicates an order in which the first data is acquired. A first terminal (102*b*) included in the plurality of terminals performs resetting of the sequence number triggered by the synchronous signal which is received by the first radio communication unit.

18 Claims, 13 Drawing Sheets

VITAL SIGNAL MEASUREMENT DEVICE, AND VITAL SIGN SIGNAL MEASUREMENT SYSTEM

TECHNICAL FIELD

The present invention relates to a vital signal measurement device and a vital signal measurement system using the same.

BACKGROUND ART

It is important to acquire vital signals daily to apply in health care, early detection of diseases, prevention of diseases, and the like. Particularly, a pulse wave propagation velocity is an important vital signal correlated with an arteriosclerosis level and a blood pressure. Therefore, measurement of the pulse wave propagation velocity is effective means when diagnosing a risk allowances in outbreak of an illness of lifestyle diseases and the like.

Here, an arteriosclerosis level and a blood pressure value greatly vary in a daily life of a test object. Therefore, measurement only performed in a resting state as in the related art is insufficient for determining risk of lifestyle diseases. In other words, for example, since states of a blood pressure and blood vessels of the test object greatly vary under variously changing environments such as a case of being exposed to rapid temperature variation, a state of lightly exercising such as jogging, a state under stress such as at work, or a state having a nightmare during sleep, it is necessary to measure the pulse wave propagation velocity in the corresponding state so as to obtain information of an arteriosclerosis level and a blood pressure value.

PTL 1 discloses a technology in which an arteriosclerosis level can be evaluated in various situations in a daily life of the test object by attaching a small and light pressure sensor to a wrist and an ankle so as not to hinder a normal life or an exercise of a test object applying no load to the test object, and continuously recording waveforms of arterial pressure by using a small-sized recording device from both sensors.

CITATION LIST

Patent Literature

PTL 1: JP-A-2011-50546

SUMMARY OF INVENTION

Technical Problem

In a case where vital signals are intended to be used for daily measurement in a daily life, in order to lighten a load to a measurement object, terminals used in measurement should be small-sized and low power consumption. Moreover, in a case of measuring a pulse wave propagation velocity, there is a need to measure waveforms of an artery by attaching the terminals to multiple sites of the body of the measurement object so as to perform communication between the terminals.

Here, the simplest method for performing communication between the terminals is to connect the terminals by wire. Meanwhile, in consideration of a load to a measurement object, it is not preferable to connect a plurality of terminals by wire. In order to prevent a normal life or an exercise of a test object, each terminal is required to be individually attached to a body, and data communication between the terminals is performed through radio communication. However, in a case of being connected through radio communication, there is a need to achieve synchronization between the terminals in order to measure an arterial propagation velocity.

If an oscillator having extremely high frequency accuracy is used so that an error of oscillation frequencies of the oscillator between the sensors can be ignored, synchronization between the terminals is not a big problem. However, when using such an oscillator, the size and cost become a problem, and thus, it is not adequate to be used for collecting data in a daily life.

In contrast, if an inexpensive and small-sized oscillator is used, synchronization between the terminals cannot be achieved, and thus, it is not possible to calculate the pulse wave propagation velocity. Moreover, when measuring the pulse wave propagation velocity, since a differential time thereof becomes information, there is a need to align not only frequencies but also time axes. Regarding a method of acquiring synchronization between the terminals which can satisfy the requirement, there is no reference in the related art. Even though PTL 1 discloses a necessity of synchronization between recording devices, there is no particular means for acquiring the synchronization disclosed.

Taking the aforementioned circumstances into consideration, the invention aims to facilitate synchronization of each terminal with respect to other terminals in a vital signal measurement system including a plurality of terminals.

Solution to Problem

In the invention disclosed in this application, an outline of a representative embodiment will be described in brief, as follows.

That is, a vital signal measurement system includes a plurality of terminals. Each of the plurality of terminals is provided with a first vital signal sensor for measuring a vital signal, a first memory for storing first data which is based on the vital signal, and a first radio communication unit for communicating with the rest of the terminals by radio. The first data is applied with a sequence number corresponding to the first data and the number indicates an order in which the first data is acquired. A first terminal included in the plurality of terminals performs resetting of the sequence number triggered by the synchronous signal which is received by the first radio communication unit.

In addition, a vital signal measurement device includes a vital signal sensor that measures a vital signal, a memory that stores data which is based on the vital signal, and a radio communication unit that communicates with the outside by radio. The data is applied with a sequence number which is a number indicating an order in which the data is acquired. The vital signal measurement device performs resetting of the sequence number triggered by the synchronous signal which is received by the radio communication unit.

Moreover, a vital signal measurement system includes a plurality of terminals. Each of the plurality of terminals is provided with a first vital signal sensor for measuring a vital signal, a first memory for storing first data which is based on the vital signal, and a first radio communication unit for communicating with the rest of the terminals by radio. A first terminal included in the plurality of terminals measures a differential time from a time when the first radio communication unit receives the synchronous signal to a feature point of the vital signal.

Advantageous Effects of Invention

In the invention disclosed in this application, to briefly describe an effect which can be achieved by a representative embodiment, it is possible to provide a vital signal measurement system which facilitates synchronization of each terminal with respect to other terminals.

DESCRIPTION OF EMBODIMENTS

Embodiment 1

Figure 1:
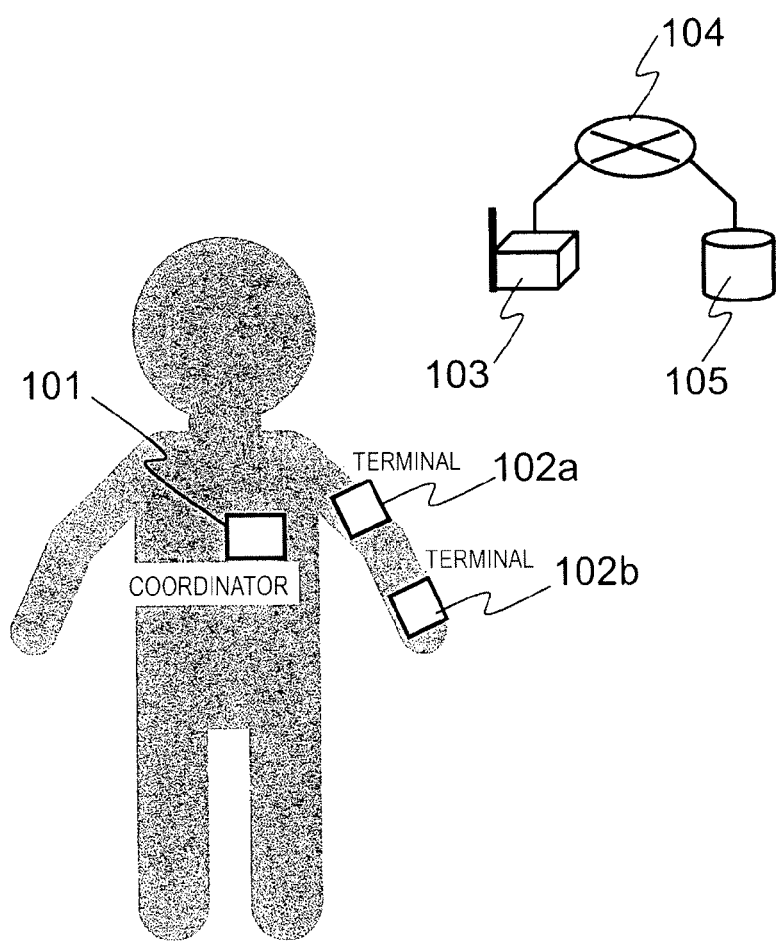
FIG. 1 is a configuration diagram of a vital signal measurement system of Embodiment 1.

A vital signal measurement system of Embodiment 1 will be described with reference to FIGS. 1 to 4. FIG. 1 is a configuration diagram of the vital signal measurement system of Embodiment 1 and is configured to have a coordinator 101, terminals 102a and 102b, a base station 103, the Internet 104, and a data server 105. Here, the subscripts a and b indicate that the elements have the same configuration. The subscript will be omitted if it is not particularly necessary to be included.

The terminal 102 is attached to a person so as to measure a vital signal. The vital signal measured by the terminal 102 is accumulated in the coordinator 101 through radio communication. The coordinator 101 performs signal processing with data of collected vital signals and transmits information of the result to the base station 103. The base station 103 is connected to the Internet 104, and its data is accumulated in the data server 105. The data accumulated in the data server 105 is used for visualization and management of health status, or application of physical examination data.

Figure 2:
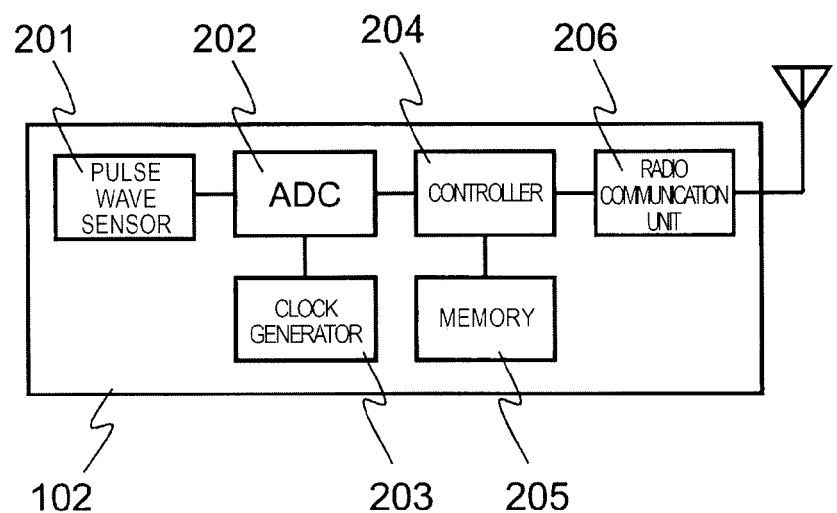
FIG. 2 is a configuration diagram of a terminal in the vital signal measurement system of Embodiment 1.

FIG. 2 is a configuration diagram of the terminal 102 in the vital signal measurement system of Embodiment 1. The terminal 102 is configured to have a pulse wave sensor 201, an analog-digital converter (ADC) 202, a clock generator 203, a controller 204, a memory 205, and a radio communication unit 206. The pulse wave sensor 201 measures a pulse wave which is a vital signal of a person. Specifically, a pulse wave sensor configured to include a pressure sensor may be pressed against the skin so as to measure skin movements occurring due to pulsation, for example. Otherwise, a photoelectric sensor may be used as the pulse wave sensor so as to measure variations in blood volume occurring due to pulsation. An ultrasonic sensor may be used as the pulse wave sensor so as to measure a pulse wave by measuring a velocity of blood flow. The pulse wave sensor is attached to an arm, a wrist, the femoral region, and an ankle.

A signal measured by the pulse wave sensor 201 is converted into a digital signal by the analog-digital converter 202. A time for conversion in which an analog signal is sampled and digitalized is controlled by a sampling clock of the clock generator 203. The converted digital signal is once accumulated in the memory 205, thereby being subjected to data transmission with respect to the coordinator 101 by the radio communication unit 206. A series of these operations is controlled by the controller 204.

Figure 3:
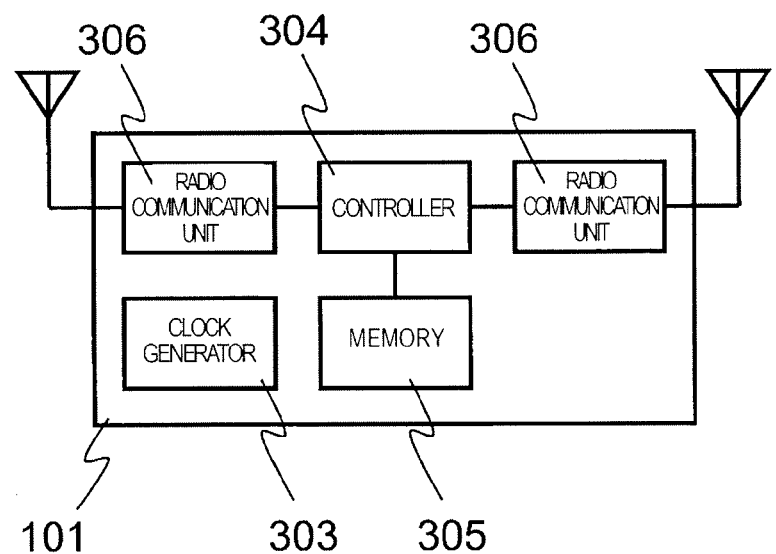
FIG. 3 is a configuration diagram of a coordinator in the vital signal measurement system of Embodiment 1.

FIG. 3 is a configuration diagram of the coordinator 101 in the vital signal measurement system of Embodiment 1. The coordinator 101 is configured to have a clock generator 303, a controller 304, a memory 305, and a radio communication unit 306. The coordinator 101 performs data communication with the terminal 102 through the radio communication unit 306. Specifically, the coordinator 101 performs data collection from the terminal 102 and controlling of the terminal 102. Data collected from the terminal 102 is once accumulated in the memory. After being subjected to necessary processing, the collected data is transmitted to the base station 103 through the radio communication unit 306. These operations are controlled by the controller 304. A required clock is supplied by the clock generator 303.

Radio communication between the coordinator 101 and the terminal 102 adopts a short distance radio communication method through a body area network having a communication range to the extent of several meters. In addition, radio communication between the coordinator 101 and the base station 103 adopts a radio communication method through a portable telephone line or a wireless LAN having a relatively wide range.

Figure 4:
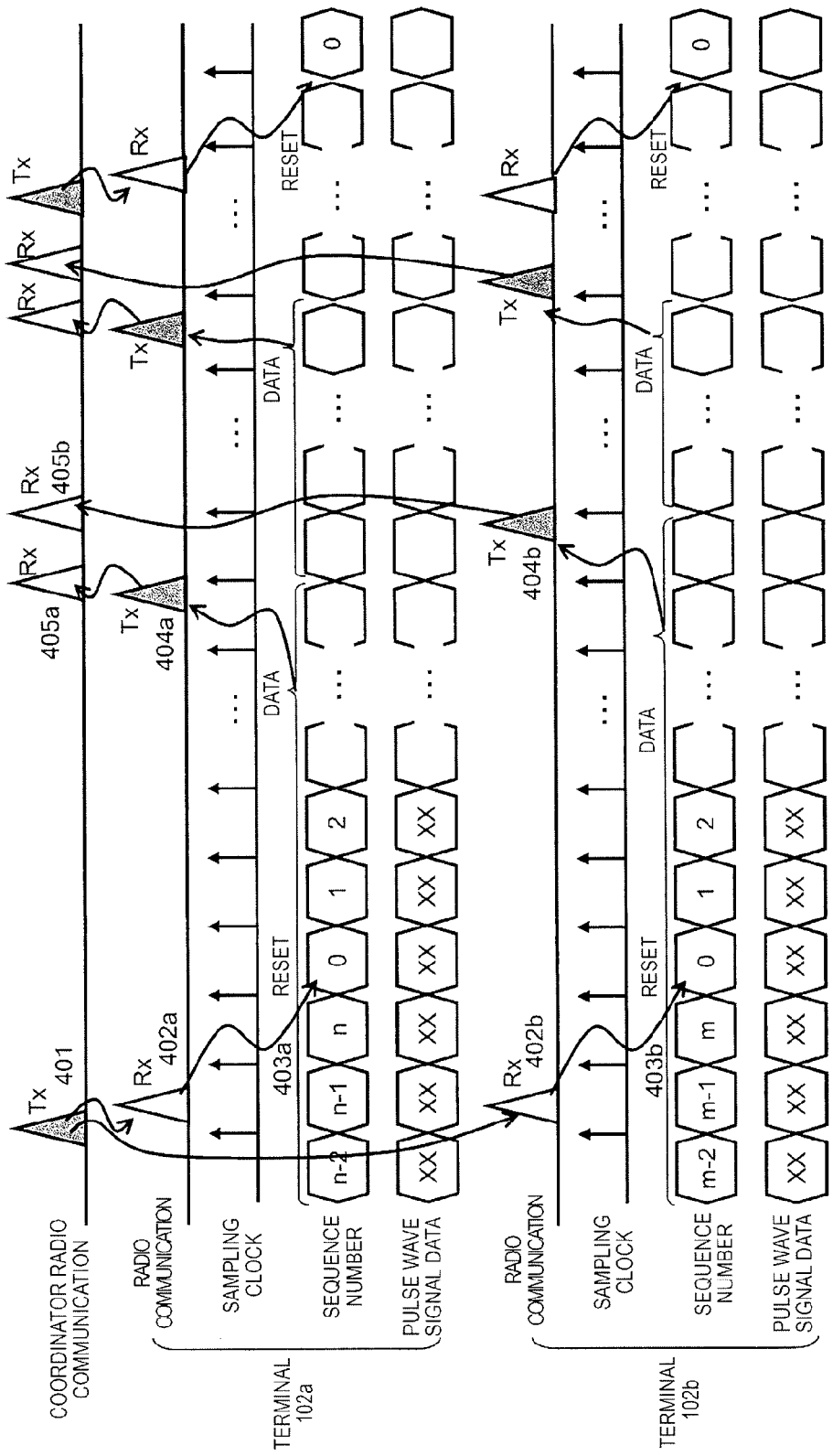
FIG. 4 is a timing chart illustrating an operation of the vital signal measurement system of Embodiment 1.

FIG. 4 is a timing chart of the vital signal measurement system of Embodiment 1. The terminal 102 measures a vital signal through the pulse wave sensor 201. Specifically, in the terminal 102, the vital signal is synchronized with a sampling clock and subjected to an analog-digital conversion, thereby being accumulated in the memory as a digital value. In this case, the terminal 102 performs sequential numbering so as to make an order (sequence) in which data is acquired recognizable, thereby storing the data in the memory 205. For example, the terminal 102 stores data having a paired sequence number and digital signal in the memory 205. Otherwise, in the sequence number, number itself does not have to be stored in the memory 205 by being caused to correspond to an address of the memory. In any case, each item of the data stored in the memory 205 is applied with the sequence number indicating an order in which data is acquired, so as to be in one-to-one correspondence with respect to each item of the data.

Generally, a frequency oscillated by a clock oscillator has frequency deviation which is an error occurring from a design value. The frequency deviation is a value which not only varies for each clock oscillator but also varies depending on operation environments such as a temperature and a power supply voltage.

Accordingly, in a plurality of the terminals, an oscillatory frequency in each clock has deviation. For example, in a case of having frequency deviation of 10 ppm, when measurement is carried out for a period of 100 seconds, there is an occurrence of deviation of 100 seconds×10 ppm=1 millisecond. In addition, for example, when a clock having deviation of 10 ppm is measured for a period of 1 hour, there is an occurrence of an error of 36 milliseconds.

When measuring a pulse wave by using the plurality of terminals and calculating a pulse wave propagation velocity, if there is such frequency deviation in a clock, time synchronization among the terminals cannot be achieved, and thus it is not possible to accurately measure a differential time necessary to calculate the pulse wave propagation velocity. In contrast, such a problem can be solved by using an accurate clock oscillator having no frequency deviation. However, such a clock oscillator is expensive and large-sized, and it is not adequate for an application in which information is regularly collected throughout the body area network. Therefore, in the invention, description will be given regarding a vital signal measurement device which can realize synchronization of data from the plurality of terminals even though a clock oscillator which is inexpensive and small-sized and has relatively greater frequency deviation is used.

The coordinator 101 transmits a synchronous signal for synchronizing the terminal 102a and the terminal 102b to the terminal 102a and the terminal 102b in a radio signal (401). Each of the terminal 102a and the terminal 102b receives the synchronous signal (402a and 402b), thereby resetting the sequence number (403a and 403b). In each of the terminal 102a and the terminal 102b, the sequence number is subjected to an increment every time data of one sample of a vital signal is acquired. Here, due to frequency deviation between a clock of the terminal 102a and a clock of the terminal 102b, there is an occurrence of gradually increasing deviation between the sequence number of the terminal 102a and the sequence number of the terminal 102b. In the invention, by performing resetting of the sequence number triggered by a synchronous signal from the coordinator 101, and thus, it is possible to achieve synchronization of a time for acquiring data between the terminals.

Incidentally, there is an occurrence of a delay time which is from when the coordinator 101 transmits the synchronous signal until the sequence number is reset in each of the terminals 102. If the terminals have the delay time different from one another, the different delay time leads to deviation of a time for resetting the sequence number. In order to avoid the deviation, it is desirable for each terminal to have an aligned delay time which is from transmit of the synchronous signal until reset of the sequence number. Use of the same hardware may solve the problem. Moreover, it is desirable to cause the delay time to be fixed by using an interruption terminal. Otherwise, the delay time may be configured to be measured in advance so that information of the difference of the delay time is recognized by the terminal 102 and the coordinator 101. In this manner, the delay time which is from when the coordinator 101 transmits the synchronous signal until the sequence number is reset in each of the terminals can be checked. Thus, it is possible to achieve synchronization of data between the terminals by performing correction. In this description, the sequence number is reset, that is, the sequence number is set to 0. However, the sequence number may be set to any particular number without being limited thereto.

The terminal 102 acquires data of a vital signal, and the data is once accumulated in the memory 205. Then, when the data is piled up to some extent, the terminal 102 creates a data packet for radio communication, thereby transmitting the data accumulated in the memory 205 to the coordinator 101 through the radio communication unit 206 (404).

The radio communication is performed by time division multiplexing. A time slot for transmitting data from the terminals 102a and 102b to the coordinator 101 is predetermined, and the transmission of data between the terminals is controlled so as not to overlap therebetween. A beacon signal used in the time division multiplexing may also be used as the synchronous signal which is used for resetting the sequence number.

In the coordinator 101, calculation of the pulse wave propagation velocity is performed based on a vital signal collected from the terminal 102. Specifically, the sequence numbers acquired from the terminals 102a and 102b are aligned, and data having the same sequence number is analyzed as data of the same time, thereby calculating a propagation time of a pulse wave between the terminals 102a and 102b. As a method of calculating the propagation time, there is a method in which a differential time of peak values of pulse waves, or a time and a correlationship of zero-cross points are analyzed. A difference of paths which are respectively from an attachment position of the terminal 102 to the terminal 102a and the terminal 102b is calculated, thereby calculating the pulse wave propagation velocity.

In this manner, the vital signal measurement system of the present embodiment includes the plurality of terminals (102). Each of the plurality of terminals is provided with a vital signal sensor (the pulse wave sensor 201) for measuring a vital signal (a pulse wave signal), the memory (205) for storing data which is based on the vital signal, and the radio communication unit (206) for communicating with the rest of the terminals by radio. The data is applied with the sequence number which is a number indicating an order in which the data is acquired. Thereafter, a first terminal (the terminal 102b) included in the plurality of terminals performs resetting of the sequence number triggered by the synchronous signal which is received by the radio communication unit.

Focusing on the terminal side, the vital signal measurement device (the terminal 102b) of the present embodiment includes the vital signal sensor (the pulse wave sensor 201) that measures a vital signal, the memory (205) that stores data which is based on the vital signal, and the radio communication unit (206) that communicates with the outside by radio. The data is applied with the sequence number which is a number indicating an order in which the data is acquired. Thereafter, the vital signal measurement device of the present embodiment performs resetting of the sequence number triggered by the synchronous signal which is received by the radio communication unit.

Focusing on the coordinator side, the coordinator (101) for the vital signal measurement device of the present embodiment includes the vital signal sensor (the pulse wave sensor 201) that measures the vital signal, the memory (205) that stores data which is based on the vital signal, and a first radio communication unit (206) that communicates with the outside by radio. The coordinator for the vital signal measurement device includes other vital signal measurement devices (102a and 102b) in which data is applied with the sequence number which is a number indicating an order in which the data is acquired, and a second radio communication unit (306) that performs radio communication. The synchronous signal which triggers resetting of the sequence number is transmitted to the vital signal measurement device (102a and 102b).

According to the above-described features, in the vital signal measurement system and the like of the present embodiment, synchronization can be achieved between the terminals even though there is frequency deviation of clocks between the terminals, and thus, it is possible to realize calculation of the pulse wave propagation velocity. In addition, it is known that a pulse wave propagation velocity is correlated with a blood pressure. Thus, a blood pressure can be calculated from the calculated pulse wave propagation velocity.

The synchronous signal from the coordinator 101 is periodically transmitted to each terminal 102. A time for transmitting the synchronous signal is determined by frequency deviation of a clock, required synchronization accuracy and the like. For example, in a case where the frequency deviation of clocks is 10 ppm and the required synchronization accuracy is 1 millisecond, when measurement continues for a period of 100 seconds, there is an occurrence of an error of 1 millisecond, it is desirable to transmit the synchronous signal at intervals of less than 100 seconds.

In the present embodiment, the description has been given regarding an example having one coordinator and two terminals. However, the embodiment is not limited thereto. The terminal may be provided three or more. In addition, a certain terminal may also have a function of the coordinator. The data collected by the coordinator has been described to be transmitted to and be accumulated in the base station and the data server. However, the embodiment is not limited thereto. For example, an application in which the coordinator analyzes data and displays a state of the pulse wave propagation velocity and a heart rate may be adopted.

Embodiment 2

Figure 5:
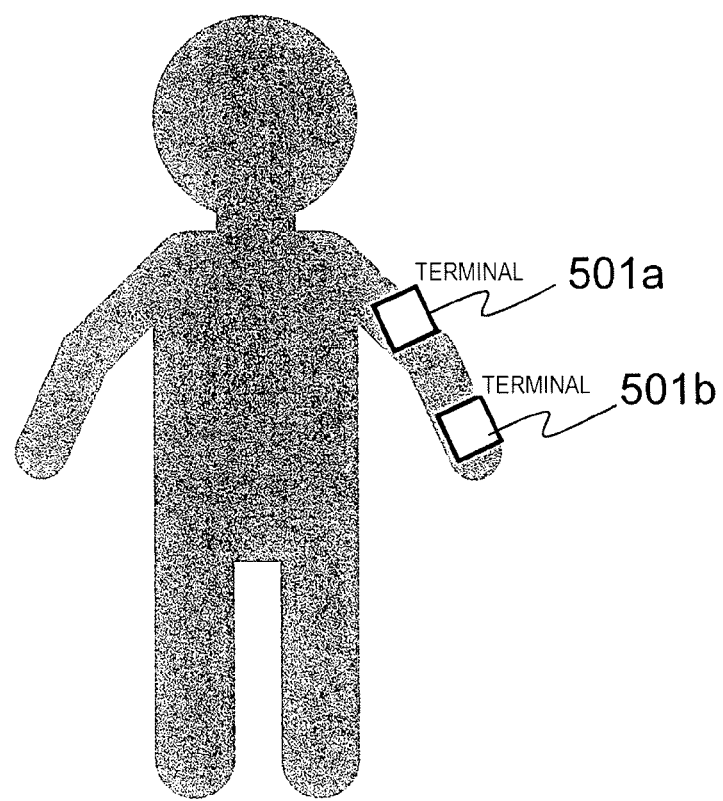
FIG. 5 is a configuration diagram of the vital signal measurement system of Embodiment 2.

The vital signal measurement device of Embodiment 2 will be described with reference to FIGS. 5 and 6. FIG. 5 is a configuration diagram of the vital signal measurement system of Embodiment 2. The vital signal measurement system of Embodiment 2 is configured to have terminals 501a and 501b. An object of the vital signal measurement system of Embodiment 2 is to achieve lower power consumption of the terminal compared to the vital signal measurement system disclosed in Embodiment 1. The configuration of the terminal is similar to the configuration of that in FIG. 2. The terminal 501a measures a vital signal, and transmits data of the vital signal to the terminal 501b. The terminal 501a transmits the synchronous signal to the terminal 501b. The synchronous signal may be the same as the data transmitted from the terminal 501a to the terminal 501b.

Figure 6:
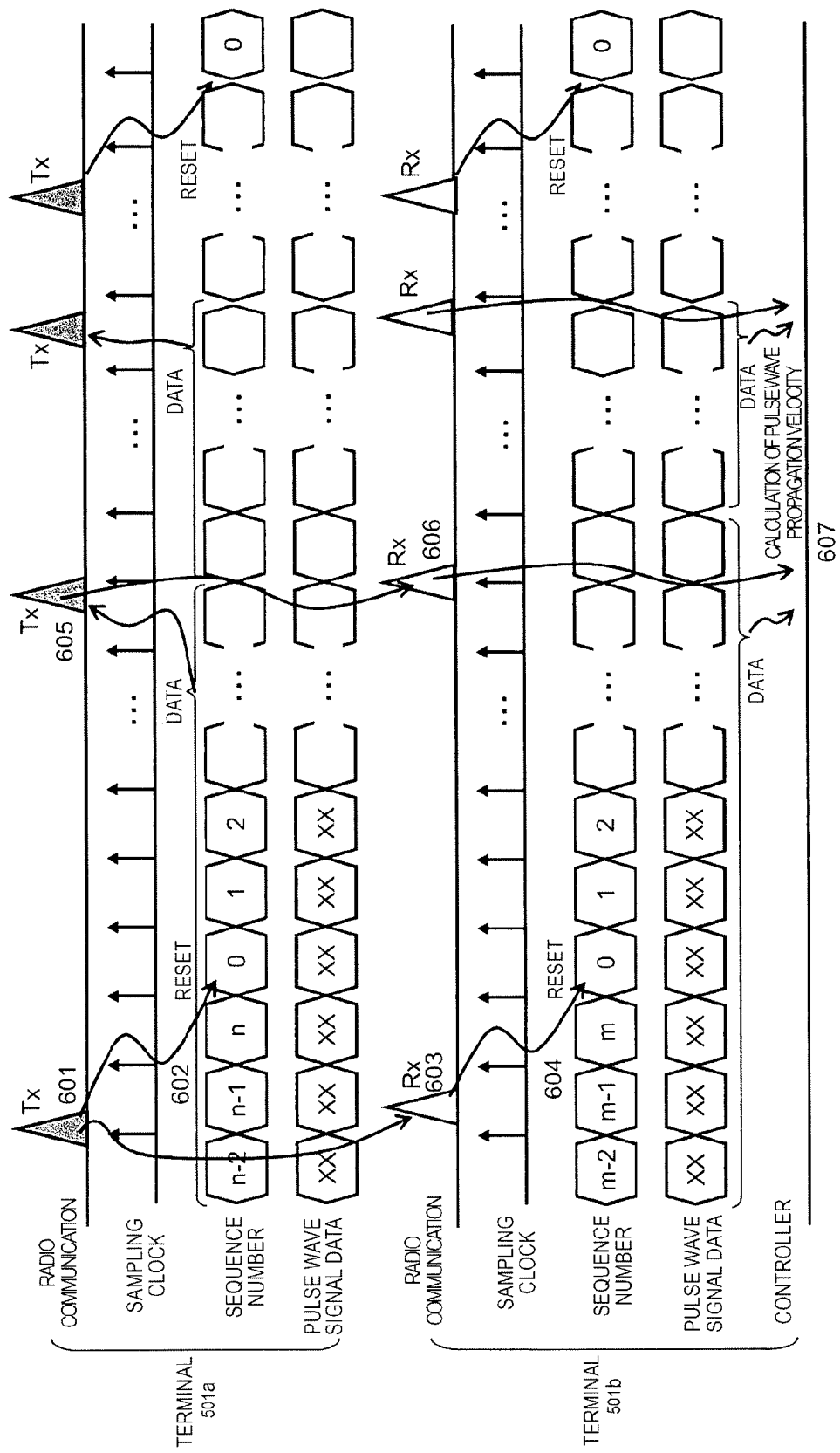
FIG. 6 is a timing chart illustrating an operation of the vital signal measurement system of Embodiment 2.

FIG. 6 is a timing chart illustrating an operation of the vital signal measurement system of the present embodiment. The terminal 501a transmits a synchronous signal to the terminal 501b (601), and performs resetting of the sequence number corresponding to an order of vital signal data triggered by the synchronous signal transmitted to the terminal 501b (602). The terminal 501b receives the synchronous signal from the terminal 501a (603), and performs resetting of the sequence number applied to the vital signal data triggered by the synchronous signal (604).

The terminal 501a measures the vital signal by using the pulse wave sensor 201, converts an analog signal to a digital signal by using the analog-digital converter 202, and once accumulates the converted signal in the memory 205. The data and the sequence number are caused to correspond to each other. Thereafter, the terminal 501a transmits the data of the measured vital signal to the terminal 501b (605). The terminal 501b receives data of the vital signal acquired by the terminal 501a (606), thereby calculating a pulse wave propagation time based on the data of the vital signal received from the terminal 501a, and the data of the vital signal measured by terminal 501b (607). In this case, the time when the sequence numbers are reset is referred to as the same time. Then, the pulse wave propagation velocity is calculated based on the calculated pulse wave propagation time and the distance between the terminals.

Since the terminal 501b is triggered by reception of the synchronous signal, and the terminal 501a is triggered by transmission of the synchronous signal transmission, there is a possibility of an occurrence of an error in the delay time until the sequence number is reset in each of the terminals. In this case, correction is performed in advance considering the delay time, thereby achieving synchronization.

In this manner, in the vital signal measurement system of the present embodiment, the second terminal (501a) transmits the synchronous signal to the first terminal (501b). Then, the second terminal performs resetting of the sequence number triggered by transmission of the synchronous signal.

According to the feature thereof, it is possible to acquire synchronization between the terminals. Therefore, even though frequency deviation is present in a clock, the pulse wave propagation velocity can be measured.

Moreover, in the vital signal measurement system of the present embodiment, data acquired by the terminal 501a is transmitted to the terminal 501b. In the present embodiment, the terminal 501a only transmits the data, and receives no radio signal. Generally, since there is a need of standby for data in order to receive a radio signal, greater power is consumed compared to transmitting thereof. In the present embodiment, since the terminal 501a only transmits the data without receiving data, it is possible to achieve low power consumption. In the vital signal measurement system, since the terminal is driven by a battery, on account of lower power consumption, it is possible to reduce the cycle of replacement or charging of a battery, to perform continuous measurement for a long time, and to decrease the battery in size.

Embodiment 3

The vital signal measurement device of Embodiment 3 will be described with reference to FIGS. 7 and 8. The system configuration of the present embodiment is to achieve further lower power consumption by reducing volume of data transmitted from a terminal 2 to a terminal 1 compared to those in Embodiment 2.

Figure 7:
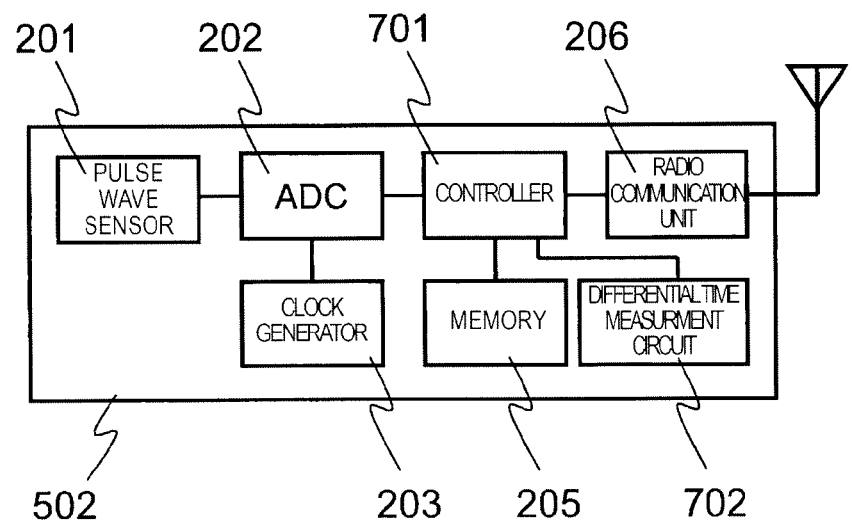
FIG. 7 is a configuration diagram of the terminal in the vital signal measurement system of Embodiment 3.

FIG. 7 is a configuration diagram of a terminal 502 used in the vital signal measurement system of Embodiment 3. The terminal 502 is configured to have the pulse wave sensor 201, the analog-digital converter (ADC) 202, the clock generator 203, a controller 701, the memory 205, the radio communication unit 206, and a differential time measurement circuit 702. The pulse wave sensor 201 is a sensor for measuring a pulse wave which is a vital signal of a person. A signal measured by the pulse wave sensor 201 is converted into a digital signal by the analog-digital converter 202. A time for converting the analog signal to be sampled and digitalized is controlled by the clock generator 203. The converted digital signal is once accumulated in the memory 205. The differential time measurement circuit 702 measures a differential time between feature points from the synchronous signal to a pulse wave signal. The feature point, for example, is a peak point of a pulse wave, or is a rising point of a pulse in a wave pulse. The radio communication unit 206 performs radio communication with other terminals. A series of these operations is controlled by the controller 701.

Figure 8:
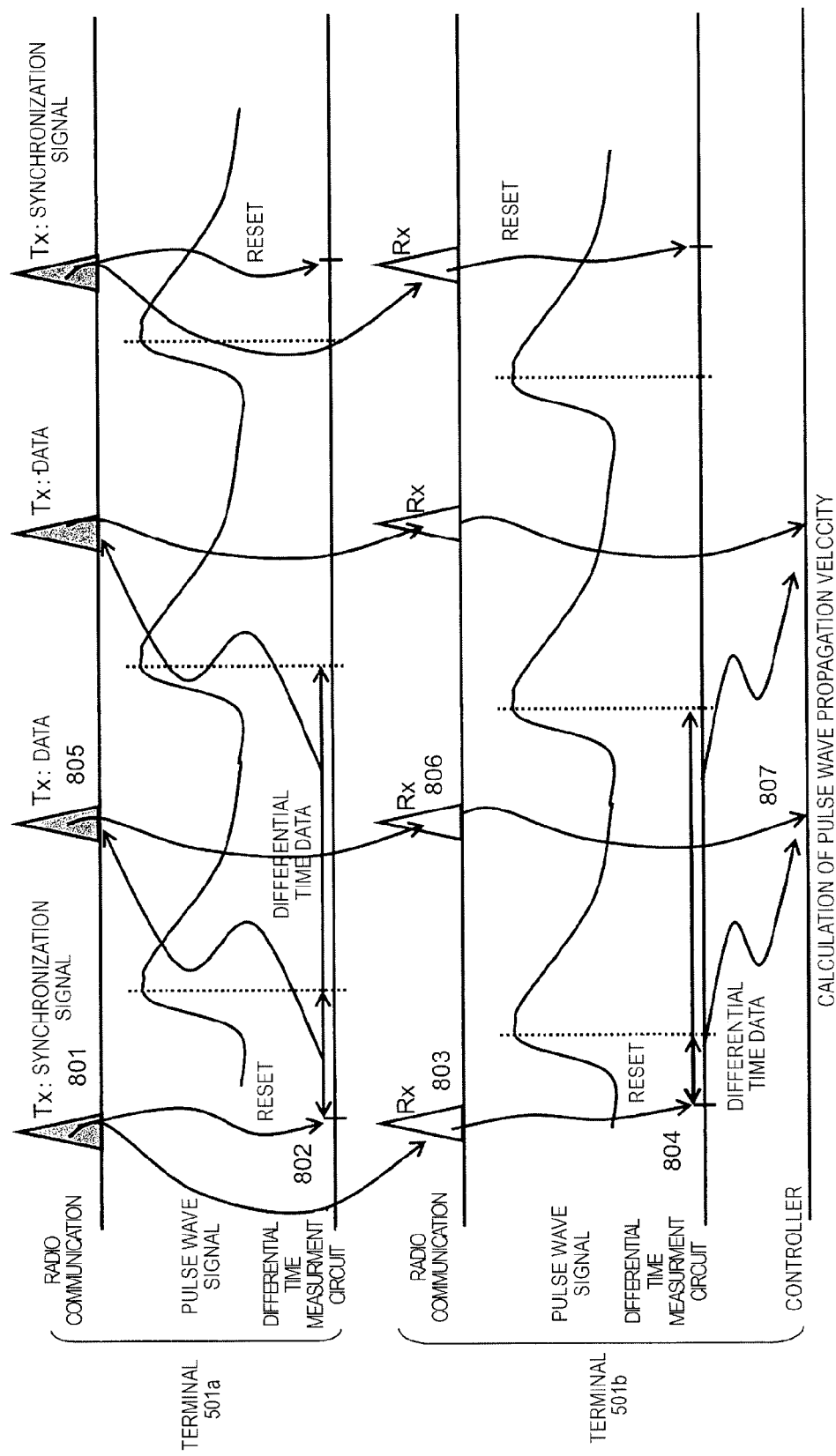
FIG. 8 is a timing chart illustrating an operation of the vital signal measurement system of Embodiment 3.

FIG. 8 is a timing chart illustrating an operation of the vital signal measurement system of Embodiment 3. The differential time measurement circuit 702 of the terminal 502a is subjected to resetting (802) triggered by a time for transmitting of the synchronous signal performed by the terminal 502a (801). Thereafter, a differential time from the reset time to the time until a pulse wave signal reaches the feature point is measured as the differential time data. That is, the differential time measurement circuit 702 measures the differential time between feature points from the synchronous signal to a pulse wave signal as the differential time data. In addition, the terminal 502b receives the synchronous signal from the terminal 501a (803) and performs resetting of the differential time measurement circuit 702. Thereafter, the terminal 502b also measures the differential time between feature points from the synchronous signal to a pulse wave signal, similar to the terminal 502a.

Then, the terminal 502a transmits the data of the measured differential time to the terminal 502b (805). The terminal 502b receives the differential time data from the terminal 502a (805), and once accumulates the data of the differential time in the memory. Thereafter, a pulse wave propagation velocity is calculated based on the differential time data from the terminal 502a and the differential time data measured by the terminal 502b.

In this manner, the vital signal measurement system of the present embodiment includes the plurality of terminals. Each of the plurality of terminals is provided with the first vital signal sensor for measuring a vital signal, the first memory for storing the first data which is based on the vital signal, and a first radio communication unit for communicating with the rest of the terminals by radio. Then, the first terminal (501b) included in the plurality of terminals measures the differential time (differential time data) from when the first radio communication unit receives the synchronous signal to the feature point of the vital signal.

According to the above-described feature, the vital signal measurement system of the present embodiment can transmit only the information of the differential time without transmitting the measured pulse wave signal, compared to Embodiment 2. By transmitting only the information of the differential time, the data volume to be transmitted can be reduced compared to a case of transmitting all the signals, thereby making lower power consumption possible. In addition, since the differential time measurement circuit is reset by the radio synchronous signal, synchronization between the terminals can be performed, and the pulse wave propagation velocity can be calculated.

In description of the present embodiment, the differential time measurement circuit performs measurement of a differential time of a digital signal. However, the embodiment is not limited thereto. The feature point may be extracted and may measure the differential time from the synchronous signal to the feature point without digitalize an analog signal measured by the pulse wave sensor.

Moreover, data of a differential time may be transmitted by radio every time being measured, or may be transmitted after the data is accumulated to some extent. In addition, the data of the measured differential time may be included in the synchronous signal to be transmitted at the same time.

In addition, functions of the terminal 1 and the terminal 2 of the present embodiment may be dynamically switched. For example, a communication direction of data may be controlled by monitoring a remaining amount of a battery so as to cause a terminal having a smaller remaining amount to be subjected to lower power consumption.

Embodiment 4

Figure 9:
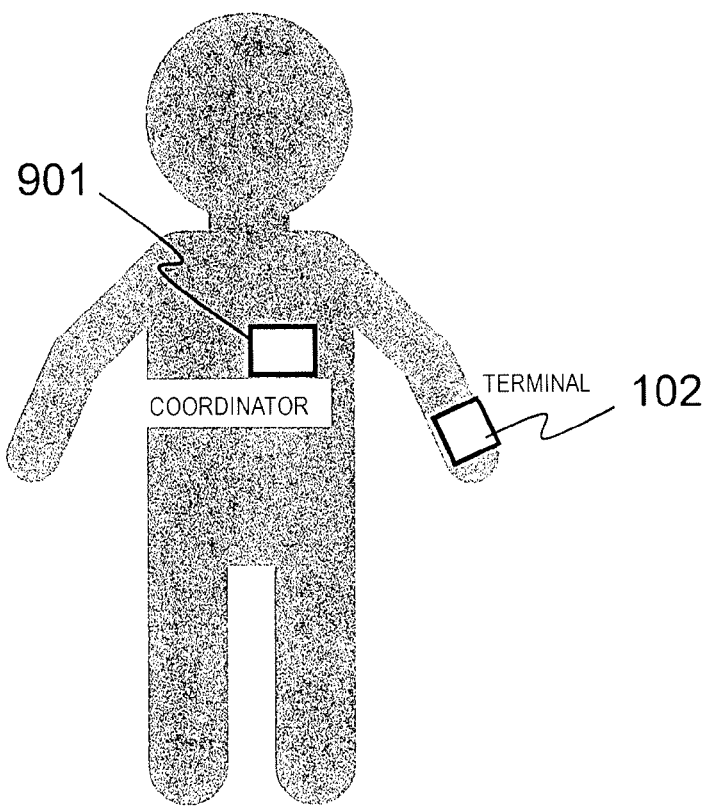
FIG. 9 is a configuration diagram of the vital signal measurement system of Embodiment 4.
Figure 10:
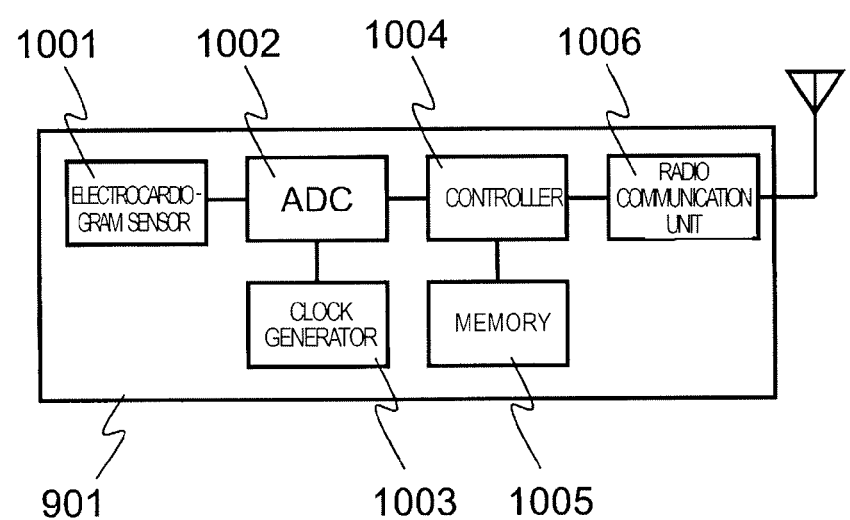
FIG. 10 is a configuration diagram of the coordinator in the vital signal measurement system of Embodiment 4.

The vital signal measurement device of Embodiment 4 will be described with reference to FIGS. 9 to 11. FIG. 9 is a configuration diagram of the vital signal measurement system of Embodiment 4. The vital signal measurement system of FIG. 9 is configured to have a coordinator 901 and the terminal 102. FIG. 10 is a configuration diagram of the coordinator 901 in the vital signal measurement system of Embodiment 4. The coordinator 901 is configured to have an electrocardiogram sensor 1001, an analog-digital converter 1002, a clock generator 1003, a controller 1004, a memory 1005, and a radio communication unit 1006.

The coordinator 901 is attached to the chest and the like of a measurement object person so as to measure an electrocardiogram of the measurement object person by using the electrocardiogram sensor 1001. The measured electrocardiogram signal is converted into a digital signal by the analog-digital converter 1002. A time for conversion in which an analog signal is sampled and digitalized is controlled by a sampling clock of the clock generator 1003. The converted digital signal is once accumulated in the memory 1005. The radio communication unit 1006 is used for communicating data with the terminal 102. The controller 1004 controls an operation of each block. In addition, the terminal 102 has a configuration similar to that of the terminal of Embodiment 1.

Figure 11:
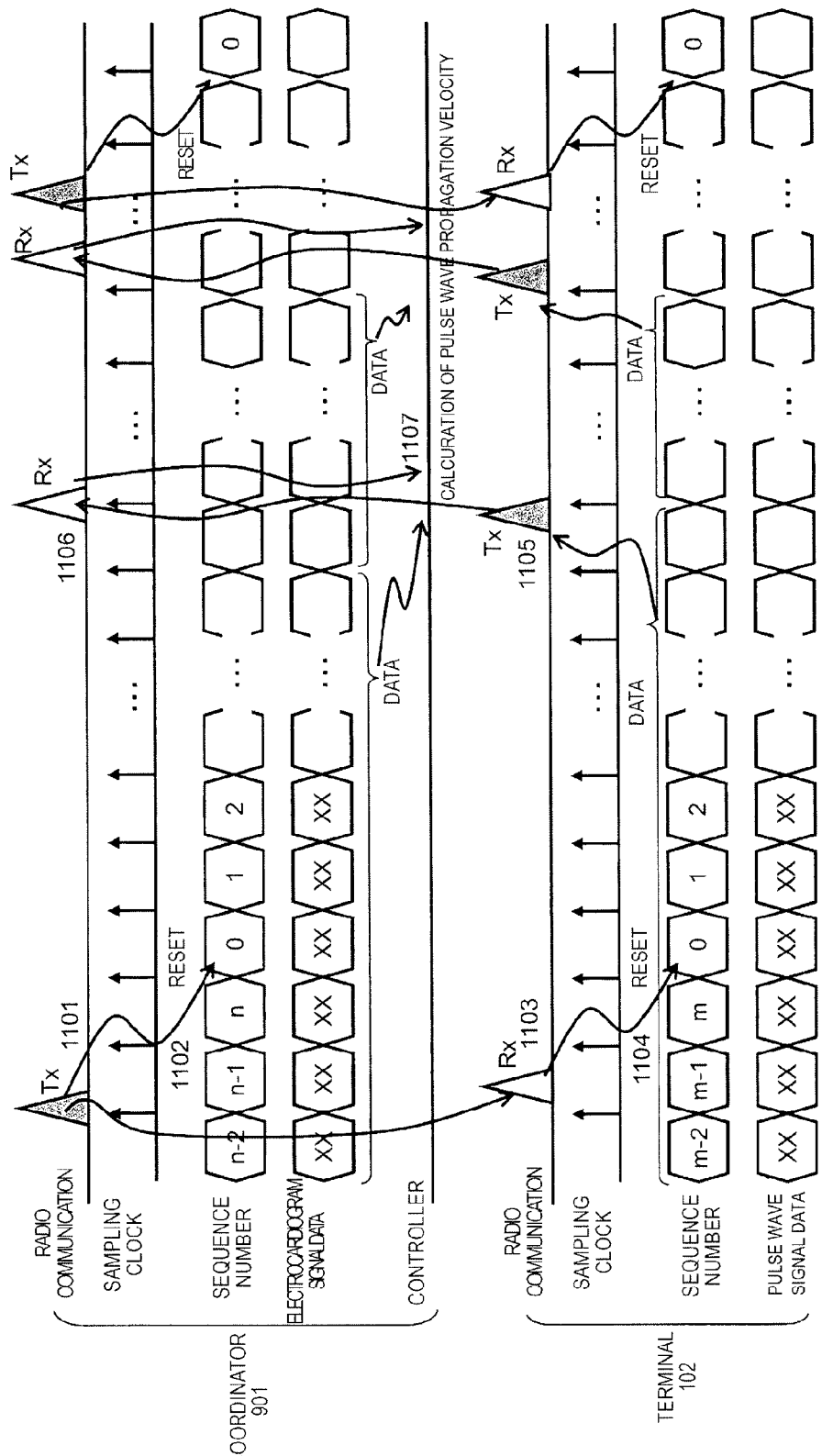
FIG. 11 is a timing chart illustrating an operation of the vital signal measurement system of Embodiment 4.

FIG. 11 is a timing chart illustrating an operation of the vital signal measurement system of Embodiment 4. The terminal 102 measures a pulse wave signal by using the pulse wave sensor 201 and performs analog-digital conversion, thereby accumulating the converted data in the memory 205. In order to acquire synchronization between the terminal 102 and the coordinator 901, the coordinator 901 transmits the synchronous signal periodically (1101). By being triggered by this synchronous signal, the coordinator 901 performs resetting of the sequence number when electrocardiogram data is acquired (1102). In addition, the terminal 102 receives the synchronous signal (1103), and performs resetting of the sequence number applied when the pulse wave data is acquired (1104).

The terminal 102 transmits data of the pulse wave signal to the coordinator 901 by radio (1105). The coordinator 901 receives data of the pulse wave signal from the terminal 102 (1106), and once stores in the memory 1005. The coordinator 901 calculates the pulse wave propagation velocity based on the data of the electrocardiogram signal stored in the memory 1005 and the data of the pulse wave signal (1107).

In this manner, in the vital signal measurement system of the present embodiment, the coordinator includes the vital signal sensor (1001) for measuring the electrocardiogram signal and the memory (1005) for storing data which is based on the electrocardiogram signal. Then, the sequence numbers in the data of the electrocardiogram signal and the data of the pulse wave signal are aligned, the data is synchronized, the feature point of the electrocardiogram signal and the feature point of the pulse wave signal are extracted from the synchronized data, thereby calculating the differential time. As the feature point, for example, a peak point, a rising point, and a falling point are used. The pulse wave propagation velocity is calculated from a position where the calculated differential time and the terminals are attached.

In this manner, by transmitting the synchronous signal from the coordinator 901, it is possible to achieve synchronization between the electrocardiogram signal measured by the coordinator 901 and the pulse wave signal measured by the terminal. Since the electrocardiogram is an electric signal for contracting the heart, the pulse wave propagation velocity can be calculated based on the electrocardiogram signal and the pulse wave signal.

In the present embodiment, an example having one terminal is described. However, the embodiment is not limited thereto. Signals from the plurality of terminals may be collected by the coordinator so as to measure the pulse wave propagation velocity in a plurality of paths. For example, in a case where two terminals including the pulse wave sensor are used, it is possible to acquire information of three paths such as two paths which are from the coordinator to each of the terminals and a path between each of the terminals. By calculating the pulse wave propagation velocity in the plurality of paths, it is possible to acquire more detailed health information of a measurement object person.

Embodiment 5

Figure 12:
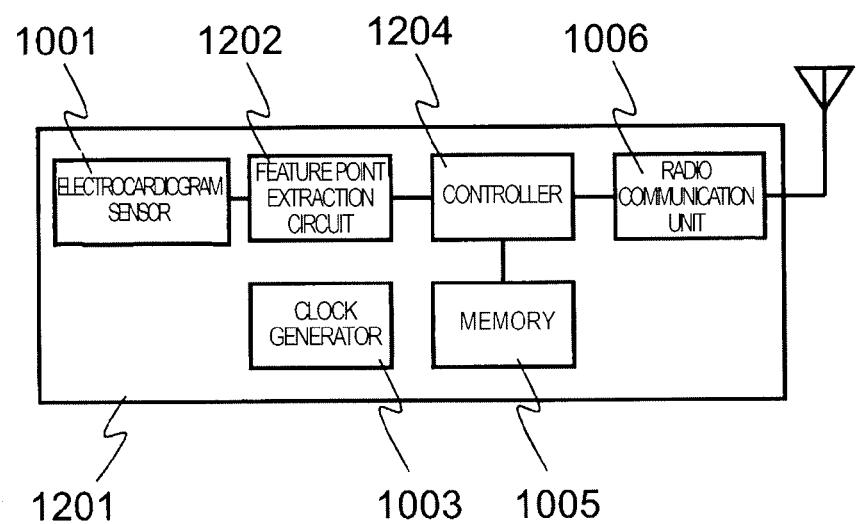
FIG. 12 is a configuration diagram of the coordinator in the vital signal measurement system of Embodiment 5.

The vital signal measurement system of Embodiment 5 will be described with reference to FIGS. 12 and 13. A configuration of the system is similar to that of Embodiment 4. FIG. 12 is a configuration diagram of the coordinator 1201 of Embodiment 5. A coordinator 1201 is configured to have the electrocardiogram sensor 1001, a feature point extraction circuit 1202, the clock generator 1003, the controller 1004, the memory 1005, and the radio communication unit 1006.

Figure 13:
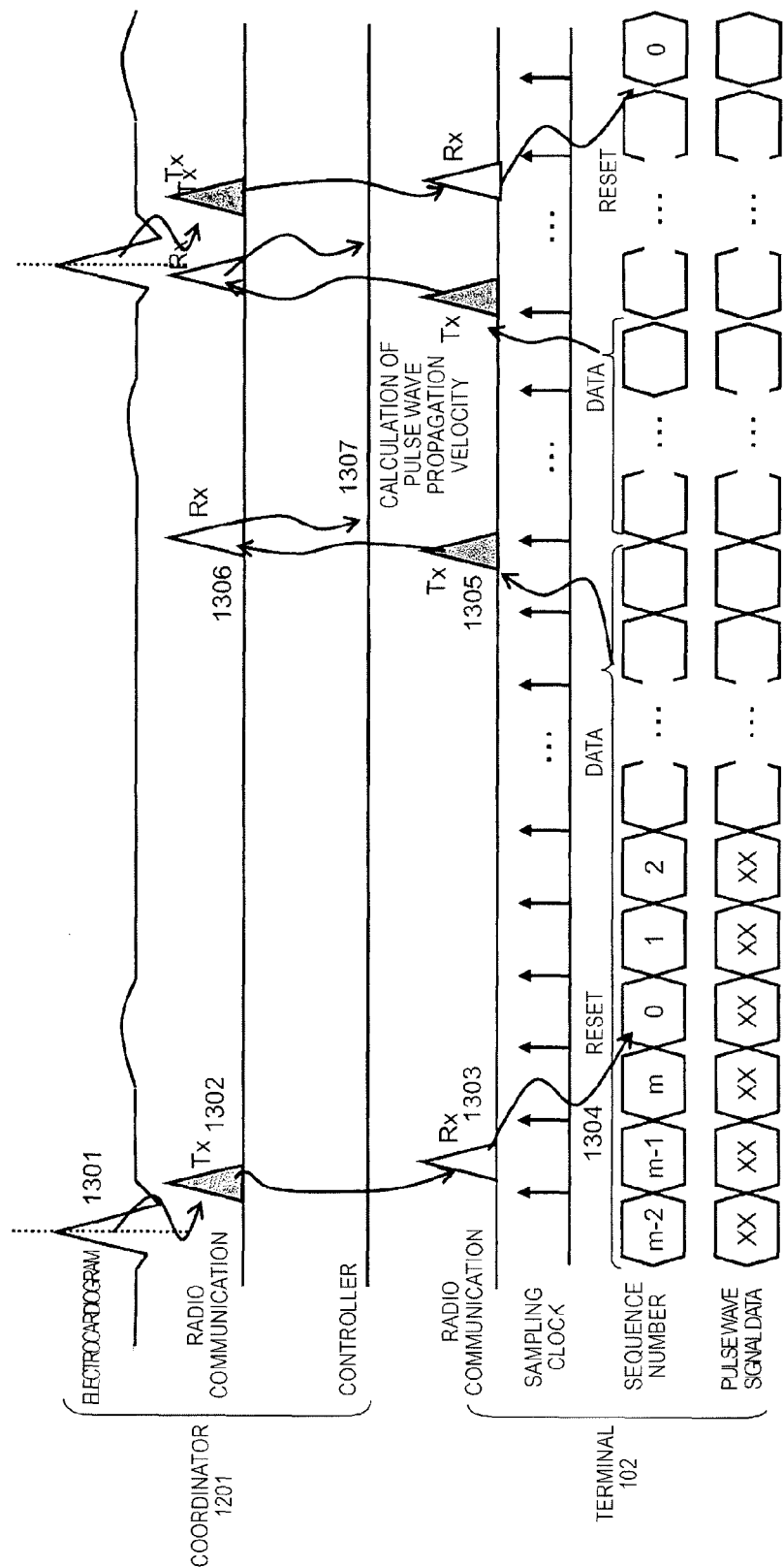
FIG. 13 is a timing chart illustrating an operation of the vital signal measurement system of Embodiment 5.

FIG. 13 is a timing chart illustrating an operation of the vital signal measurement system of Embodiment 5. The coordinator 1201 measures the electrocardiogram signal by using the electrocardiogram sensor 1001. The feature point extraction circuit 1202 extracts a feature point of the measured electrocardiogram signal. By being triggered by extraction of the feature point (1301), the synchronous signal is transmitted from the radio communication unit 1006 (1302). The terminal 102 receives the synchronous signal (1303), thereby performing resetting of the sequence number (1304). That is, in the vital signal measurement system of the present embodiment, resetting of the sequence number of the data of the terminals is performed triggered by feature point of the electrocardiogram signal.

The terminal 102 measures the pulse wave signal and transmits the measure data to the coordinator 1201 through radio communication (1305). The coordinator 1201 receives a signal from the terminal 102 (1306), thereby calculating the pulse wave propagation velocity using the data (1307).

In this manner, in the vital signal measurement system of the present embodiment, in accordance with transmission of the synchronous signal with respect to the terminals performed by the coordinator triggered by the electrocardiogram signal, a zero point of the sequence number becomes meaningful. Therefore, without being compared to the data of the pulse wave signal, the data of the electrocardiogram signal is accumulated in the memory, and the sequence number of the feature point of the pulse wave signal becomes the differential time from the feature point of the electrocardiogram signal. Accordingly, the coordinator can calculate the pulse wave propagation velocity by extracting the sequence number of the feature point of the pulse wave signal.

In the present embodiment, the terminals transmit the data of the pulse wave signal to the coordinator. However, the embodiment is not limited thereto. The terminal may include a feature point extraction circuit of the pulse wave signal and transmit only the sequence number corresponding to the feature point to the coordinator. In this manner, the data volume of radio communication can be greatly decreased, thereby making lower power consumption possible.

Embodiment 6

Figure 14:
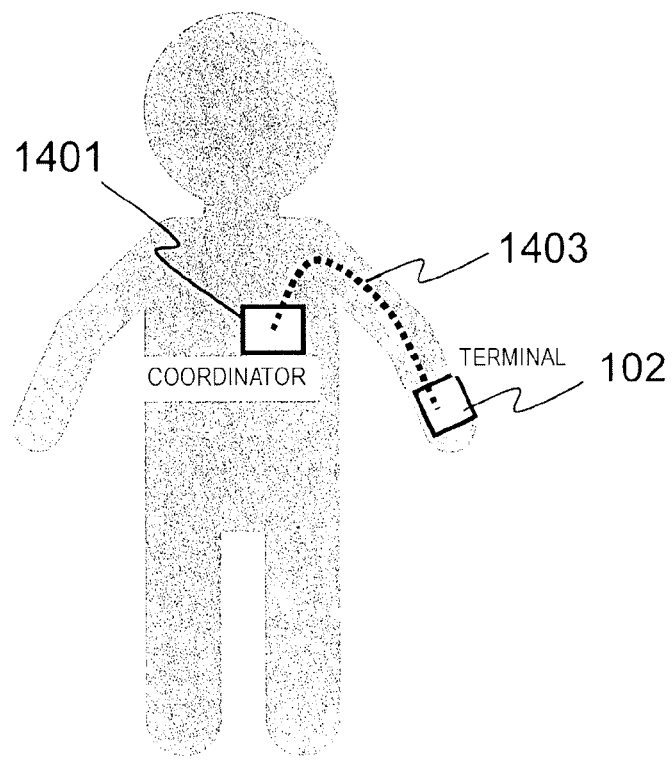
FIG. 14 is a configuration diagram of the vital signal measurement system of Embodiment 6.
Figure 14:
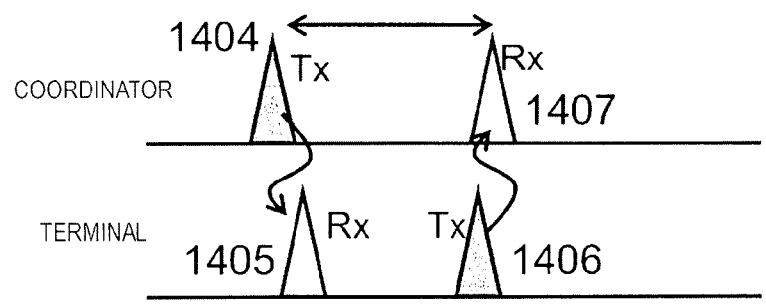
Figure 15:
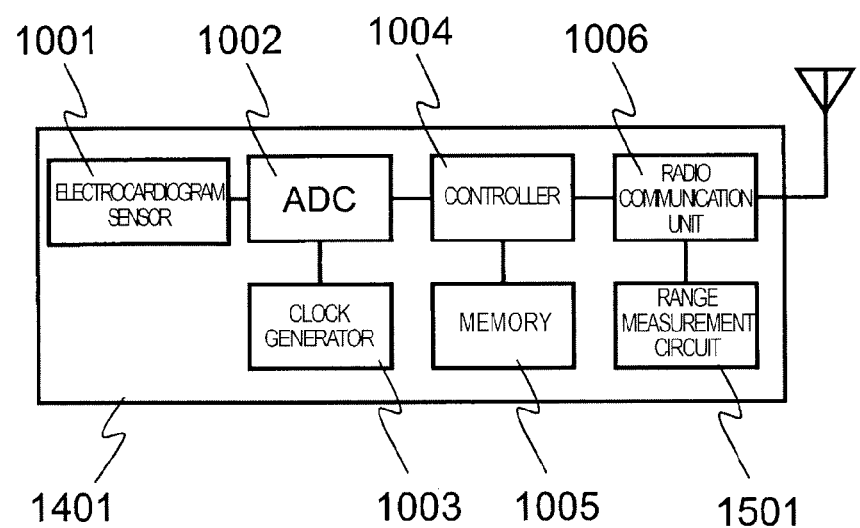
FIG. 15 is a configuration diagram of the coordinator in the vital signal measurement system of Embodiment 6.

The vital signal measurement system of Embodiment 6 will be described with reference to FIGS. 14 and 15. FIG. 14 is a configuration diagram of the vital signal measurement system of Embodiment 6, and FIG. 15 is a configuration diagram of the coordinator in the vital signal measurement system of Embodiment 6. The coordinator of the present embodiment includes a range measurement circuit 1501 for measuring a range. The radio communication unit 1006 adopts human body communication. Human body communication is a communication method having a human body as a propagation path. In this manner, if human body communication is adopted as a radio communication unit, and range measurement by radio is further performed, it is possible to calculate a path (1403) between the terminals along a human body.

As a method of measuring a range, there is a method of using a propagation differential time and a method of using receiving power. In the range measurement by the propagation differential time, firstly, a coordinator 1401 transmits a radio signal (1404), and then, the terminal 102 receives the radio signal (1405). The terminal 102 which receives the radio signal returns the radio signal back to the coordinator 1401 (1406). The coordinator 1401 receives the radio signal from the terminal 102 (1407), and measures the differential time from when the radio signal is transmitted until when the radio signal is received. Processing time of the terminal 102 is subtracted from the measured differential time and divide the subtracted value by 2, and thus, it is possible to obtain the propagation time through which radio communication is propagated in a range from the coordinator 1401 to the terminal 102. The obtained propagation time is divided by a velocity of a radio signal, and thus, it is possible to calculate the range between the coordinator 1401 and the terminal 102.

When the coordinator 1401 receives a radio signal transmitted by the terminal 102, the range can be estimated by measuring intensity of the radio signal. In this method, intensity of the received signal is measured so as to calculate the range, since intensity of the radio signal is attenuated being inversely proportional to a propagation range.

In this manner, in the vital signal measurement system of the present embodiment, a distance between the coordinator 1401 and the terminal 102 of the path along a body of a measurement object is calculated. In this manner, the pulse wave propagation velocity can be calculated by measuring a propagation range together with a pulse wave propagation time.

Hereinabove, the invention made by this inventor has been described in detail with reference to the embodiments. However, the invention is not limited to the embodiments, and it is not necessary to mention that various changes can be made without departing from the spirit and the scope thereof.

REFERENCE SIGNS LIST

101 . . . coordinator, 101a and 101b . . . terminal, 103 . . . base station, 104 . . . Internet, 105 . . . data server, 201 . . . pulse wave sensor, 202 . . . analog-digital converter (ADC), 203 . . . clock generator, 204 . . . controller, 205 . . . memory, 206 . . . radio communication unit, 303 . . . clock generator, 304 . . . controller, 305 . . . memory, 306 . . . radio communication unit, 501a and 501b . . . terminal, 502 . . . terminal, 701 . . . controller, 702 . . . differential time measurement circuit, 901 . . . coordinator, 1001 . . . electrocardiogram sensor, 1002 . . . analog-digital converter, 1003 . . . clock generator, 1004 . . . controller, 1005 . . . memory, 1006 . . . radio communication unit, 1201 . . . coordinator, 1202 . . . feature point extraction circuit, 1401 . . . coordinator, 1501 . . . range measurement circuit

The invention claimed is:

1. A vital signal measurement system, comprising:
a plurality of terminals,
wherein each of the plurality of terminals is provided with a first vital signal sensor for measuring a vital signal, a first memory for storing first data which is based on the vital signal, and a first radio communication unit for communicating with the rest of the terminals by radio,
wherein the first data is applied with a sequence number corresponding to the first data and the number indicates an order in which the first data is acquired, and
wherein a first terminal included in the plurality of terminals performs resetting of the sequence number triggered by a synchronous signal which is received by the first radio communication unit; and
a coordinator that is provided with a second radio communication unit for communication with each of the plurality of terminals by radio,
wherein the coordinator transmits the synchronous signal to each of the plurality of terminals,
wherein each of the first vital signal sensors is a sensor for measuring a pulse wave signal, and
wherein the coordinator is further provided with a second vital signal measurement sensor for measuring an electrocardiogram signal and a second memory for storing second data which is based on the electrocardiogram signal.

2. The vital signal measurement system according to claim 1,
wherein the first data having the same sequence number is data of the same time in an analysis performed in each of the plurality of terminals.

3. The vital signal measurement system according to claim 2,
wherein each of the first vital signal sensors is a sensor for measuring a pulse wave signal, and
wherein the analysis is a calculation of the pulse wave propagation velocity.

4. The vital signal measurement system according to claim 1,
wherein the coordinator performs transmission of the synchronous signal triggered by the electrocardiogram signal.

5. The vital signal measurement system according to claim 4,
wherein the coordinator is further provided with a range measurement circuit for measuring a range of radio communication between the coordinator and the terminal based on the first data and the second data.

6. The vital signal measurement system according to claim 1,
wherein each of the plurality of terminals transmits the first data and the sequence number to the coordinator.

7. A vital signal measurement system, comprising:
a plurality of terminals,
wherein each of the plurality of terminals is provided with a first vital signal sensor or measuring a vital signal, a first memory for storing first data which is based on the vital signal, and a first radio communication unit for communicating with the rest of the terminals by radio,
wherein the first data is applied with a sequence number corresponding to the first data and the number indicates an order which the first data acquired, and
wherein a first terminal included in the plurality of terminals performs resetting of the sequence number triggered by a synchronous signal which is received by the first radio communication unit,
wherein a second terminal which is a terminal included in the plurality of terminals and is different from the first terminal transmits the synchronous signal to the first terminal, and
wherein the second terminal performs resetting of the sequence number triggered by transmission of the synchronous signal.

8. The vital signal measurement system according to claim 7,
wherein the second terminal further transmits the first data acquired by the second terminal to the first terminal.

9. The vital signal measurement system according to claim 1,
wherein each of the plurality of terminals is further provided with a clock generation circuit for generating a sampling clock and an analog-digital converter for converting an analog signal which is based on the vital signal into the first data which is a digital signal for each sampling clock, and applies the sequence number to the first data acquired for each sampling clock.

10. A vital signal measurement system, comprising:
a plurality of terminals,
wherein each of the plurality of terminals is provided with a first vital signal sensor for measuring a vital signal, a first memory for storing first data which is based on the vital signal, and a first radio communication unit for communicating with the rest of the terminals by radio,
wherein a first terminal included in the plurality of terminals measures a differential time from a time when the first radio communication unit receives a synchronous signal to a feature point of the vital signal,
wherein a second terminal which is a terminal included in the plurality of terminals and is different from the first terminal transmits the synchronous signal to the first terminal, and
wherein the second terminal performs resetting of a sequence number triggered by transmission of the synchronous signal.

11. The vital signal measurement system according to claim 10,
wherein the second terminal further transmits the first data acquired by the second terminal to the first terminal.

12. The vital signal measurement system according to claim 10,
wherein each of the plurality of terminals is further provided with a clock generation circuit for generating a sampling clock and an analog-digital converter for converting an analog signal which is based on the vital signal into the first data which is a digital signal for each sampling clock, and applies the sequence number to the first data acquired for each sampling clock.

13. The vital signal measurement system according to claim 10,
wherein the first data is applied with a sequence number corresponding to the first data and the number indicates an order in which the first data is acquired.

14. The vital signal measurement system according to claim 13,
wherein the first data having the same sequence number is data of the same time in an analysis performed in each of the plurality of terminals.

15. The vital signal measurement system according to claim 14,
wherein each of the first vital signal sensors is a sensor for measuring a pulse wave signal, and
wherein the analysis is a calculation of the pulse wave propagation velocity.

16. The vital signal measurement system according to claim 7,
wherein each of the plurality of terminals is further provided with a clock generation circuit for generating a sampling clock and an analog-digital converter for converting an analog signal which is based on the vital signal into the first data which is a digital signal for each sampling clock, and applies the sequence number to the first data acquired for each sampling clock.

17. The vital signal measurement system according to claim 7,
wherein the first data having the same sequence number is data of the same time in an analysis performed in each of the plurality of terminals.

18. The vital signal measurement system according to claim 17,
wherein each of the first vital signal sensors is a sensor for measuring a pulse wave signal, and
wherein the analysis is a calculation of the pulse wave propagation velocity.

* * * * *